United States Patent [19]

Smythe et al.

[11] Patent Number: 5,068,443

[45] Date of Patent: Nov. 26, 1991

[54] PROCESS FOR THE MANUFACTURE OF 2,6-DICHLORO-4-NITROANILINE

[75] Inventors: Stephen R. Smythe, North Muskegon; Martin G. Cole, Spring Lake; James S. Grier, Whitehall, all of Mich.

[73] Assignee: NorAm Chemical Company, Wilmington, Del.

[21] Appl. No.: 532,035

[22] Filed: Jun. 1, 1990

[51] Int. Cl.$^5$ .............................................. C07C 209/74
[52] U.S. Cl. .................................................... 564/496
[58] Field of Search ........................................ 564/496

[56] References Cited

U.S. PATENT DOCUMENTS

| | | | |
|---|---|---|---|
| 4,172,098 | 10/1979 | Scheuermann et al. | 260/646 |
| 4,414,415 | 11/1983 | Aubouy et al. | 564/412 |
| 4,605,767 | 8/1986 | Arndt et al. | 564/412 |
| 4,613,698 | 9/1986 | Arndt et al. | 564/412 |

FOREIGN PATENT DOCUMENTS

| | | |
|---|---|---|
| 2648054 | 4/1976 | Fed. Rep. of Germany . |
| 56-36435 | 4/1981 | Japan . |
| 1108375 | 4/1968 | United Kingdom . |
| 1587965 | 4/1981 | United Kingdom . |

OTHER PUBLICATIONS

Chattaway et al., J. Chem. Soc. 125, p. 1196.

*Primary Examiner*—Richard L. Raymond
*Attorney, Agent, or Firm*—Connolly and Hutz

[57] ABSTRACT

The present invention is directed to a process for the chlorination of nitroaniline compounds with $Cl_2$ in a reaction medium containing acetic acid. A process for the chlorination of nitroaniline with $Cl_2$ in a reaction medium which has been recycled from a prior chlorination is also described.

14 Claims, No Drawings

PROCESS FOR THE MANUFACTURE OF 2,6-DICHLORO-4-NITROANILINE

The present invention relates to a process for the chlorination of nitroanilines which reduces or eliminates the generation of noxious aqueous effluent and its related disposal problems and provides for a chlorination process which includes the reuse of the reaction medium.

BACKGROUND OF THE INVENTION

Nitroanilines having chlorine substituents have been used as starting materials for a variety of products such as drugs, dyes and pesticides, e.g., 2,6-dichloro-4-nitroaniline (DCNA), is known to be active against certain soil, foliar and fruit pathogens on ornamental and agricultural crops.

In general, the prior processes used aqueous solutions of the strong inorganic acids such as hydrochloric or hypochlorous acid or their salts such as alkali hypochlorite. Subsequent treatments of the product are typically performed with relatively large volumes of aqueous solutions. The resulting aqueous effluent is a potential environmental pollutant which must be processed prior to disposal. The processing of the total aqueous effluent can be time consuming and represents an additional cost in the manufacture of the chlorinated products. Furthermore, the combined volume of aqueous effluent from the reaction itself and the subsequent washings of the product are difficult to process for recycling. It would be desirable to have a process for chlorinating nitroanilines which produces minimal aqueous effluent and provides a product which can be handled in a convenient, economical manner. It would also be desirable to have a method of reusing the reaction effluent in subsequent reactions.

The object of this invention is to provide a process for the chlorination of nitroaniline which reduces or eliminates noxious aqueous effluent and its related disposal problems.

It is a further object of this invention to provide a process for the chlorination of nitroanilines wherein the effluent is conveniently reused in subsequent chlorination reactions.

SUMMARY OF THE INVENTION

The present invention is directed to a process for the chlorination of nitroaniline compounds with chlorine in a reaction medium containing acetic acid. A process for the chlorination of nitroaniline with chlorine in a reaction medium which has been recycled from a prior chlorination is also described.

DETAILED DESCRIPTION OF THE INVENTION

This invention is a process for the chlorination of nitroaniline with chlorine ($Cl_2$) in a reaction medium of acetic acid. The use of acetic acid in place of strong inorganic acids reduces or eliminates the aqueous effluent which results from the use of strong inorganic acid solutions.

Another aspect of this invention is a process for the chlorination of nitroaniline with $Cl_2$ in a reaction medium which has been recycled from a prior chlorination.

According to the process of this invention, substituted or unsubstituted nitroaniline is chlorinated with $Cl_2$ in a reaction medium containing acetic acid. It has been found that portions or all of the strong inorganic acids used in the prior art processes can be replaced with acetic acid. The concentration of acetic acid is expressed as a weight percent is based on the weight of the reaction medium prior to the addition of the reactants and other components of the reaction mixture such as hydrogen chloride or chlorine gases. As the concentration of acetic acid is increased, the amount of strong acid can be reduced until it is essentially eliminated.

Chlorinated nitroanilines having desirable handling characteristics have been obtained in good yields using reaction mediums containing about 15 weight percent acetic acid. The remaining portion of such a medium comprises an aqueous solution of a strong inorganic acid such as hydrochloric acid. When acetic acid is part of the reaction medium, it is possible to obtain product with good handling characteristics. It has been found that as the percent of acetic acid is increased, the product has improved purity and handling when compared to product produced at a comparable temperature using only a strong inorganic acid solution. The reaction product made in an acetic acid medium is convenient to handle because the crystal size is larger, therefore it filters quickly and can be more easily dewatered depending upon how much water was present in the medium. The products of the process of this invention show improvement in ease of stirring the slurry, the ease of washing the cake and the drying, packaging and formulation of the final product. Also, less water is required in the subsequent treatment of the reaction products of the process of the invention. However, the presence of an aqueous acid solution gives rise to the effluent problems discussed previously. In the preferred embodiment of this invention, the reaction medium consists essentially of acetic acid in order to eliminate as much water as possible. Glacial acetic acid which is typically about 99 weight percent acetic acid is particularly preferred as the reaction medium.

Typically, the mole ratios of the reactants can be varied depending upon the degree of chlorination desired for a specific substituted or unsubstituted nitroaniline reactant. Specifically, when the dichlorinated derivative is desired, the molar ratio of chlorine to substituted or unsubstituted nitroaniline can range from about 0.95 to about 2.2. When the unsubstituted nitroaniline is used as the starting material, the molar ratio is preferably from about 1.8 to about 2.5 and most preferably about 1.9 to about 2.0.

Substituted or unsubstituted nitroaniline compounds or the hydrochloride salts thereof which are useful in the process of this invention are compounds of the formula:

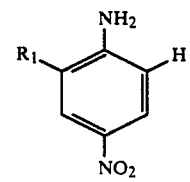

wherein $R_1$ is chloro or hydrogen.

The chlorinating agent is typically $Cl_2$ and can be used in the form of a gas or as a solution of chlorine gas in glacial acetic acid. Hydrogen chloride gas is typically added to the reaction mixture because it prevents undesirable reactions and improves the reaction rate. The process according to the present invention is typically carried out at a temperature of from about 16° C. to about 100° C. Use of the lower temperatures is more economical and has less likelihood of undesirable side reactions. In balancing the need for high yield, high purity and a reasonable reaction time, the chlorination is preferably carried out at a temperature of from about 20° C. to about 65° C.

In a more detailed description of a typical process according to this invention, the nitroaniline is added to the reaction medium containing acetic acid and the resulting slurry is stirred. Hydrogen chloride gas is added with external cooling to keep the temperature of the reaction at the desired level. Chlorine gas is then added to the mixture while cooling the reaction mixture to maintain the temperature at the desired level. After a postreaction stir time, the reaction mixture is cooled and filtered and the product is dried in vacuo.

Products of the process of this invention include 6-chloro-2,4-dinitroaniline, 2,4-dichloro-6-nitroaniline, and 2-chloro-4-nitroaniline. The compound, 2,6-dichloro-4-nitroaniline is particularly preferred as the product of this process.

In general, the use of aqueous solutions containing strong inorganic acids such as hydrochloric or hypochlorous acid or their salts such as alkali hypochlorite produces aqueous effluent which must be processed prior to disposal. Subsequent treatments of the chlorinated product typically require relatively large volumes of aqueous solutions. The processing of the total aqueous effluent can be time consuming and represents an additional cost in the manufacture of the desired products. Furthermore, the combined volume of aqueous effluent from the reaction itself and the subsequent washings of the product makes it difficult to process for recycling.

It has been found that the effluent of the chlorination of substituted or unsubstituted nitroanilines in a reaction medium containing at least about 15 weight percent acetic acid can be reused in subsequent chlorination reactions to produce products of acceptable quality. More specifically, in a first cycle, a substituted or unsubstituted nitroaniline can be chlorinated with $Cl_2$ in a reaction medium containing acetic acid wherein the concentration of acetic acid is at least 15 weight percent based on the total weight of the reaction medium prior to the addition of the remainder of the reaction mixture. The effluent resulting from the reaction is recycled into the reactor and sufficient acetic acid is added to bring the acetic acid concentration in the reactor to at least about 15 weight percent. A substituted or unsubstituted nitroaniline is added to the reactor and chlorinated with $Cl_2$. Upon essential completion of the chlorination the reaction mixture is then cooled and processed in the usual manner.

In a preferred process, the acetic acid concentration in the first cycle is at least about 30 weight percent and the acetic acid concentration in the effluent produced is at least 15 weight percent. In order to essentially eliminate water in the effluent, the acetic acid concentration can be about 99 weight percent in which case, the acetic acid concentration of the effluent is adjusted to at least 80 weight percent for the subsequent chlorination.

When the lower concentrations of acetic acid are used, the chlorination reactions can be performed at temperatures from about −5° C. to the boiling point of the reaction medium, preferably from about 15° C. to about 100° C. Some heat treatment of the reaction mixture containing the recycled effluent is performed to improve handling characteristics.

The following examples illustrate the process according to the invention without limiting it thereto. Parts denotes parts by weight. The yield is the isolated chemical yield based on the moles of desired product actually produced as a percentage of the moles of the nitroaniline.

EXAMPLES

Example 1

Fifty grams of p-nitroaniline, 397 grams of concentrated hydrochloric acid and 174 grams of glacial acetic acid were charged to a 1 liter flanged flask fitted with a gas inlet tube, a thermocouple, a mechanical stirrer and a condenser venting to a recirculating NaOH scrubber.

The reagents were mixed thoroughly and the flask immersed in a water cooling bath to lower the temperature to 16° C. Chlorine (54.7 g) was added over four hours. The temperature during the chlorination was maintained between 16° C. and 20° C. with the water bath. The resultant thick yellow slurry was filtered in a sintered glass funnel. The cake was washed with a concentrated hydrochloric acid/glacial acetic acid mixture and water at room temperature. The washed cake was dried to yield DCNA (69.7 g; 92.3% weight yield) as a yellow powder.

Example 2

A slurry of 81.3 parts p-nitroaniline in 828.4 parts of glacial acetic acid was stirred in a 1 liter round bottomed flask, equipped with thermocouple, mechanical stirrer, a sparge tube and a vent system.

Hydrogen chloride gas (12.6 parts) was sparged into the slurry. Chlorine (82.1 parts) was sparged into the mixture while cooling to maintain the temperature at about 30° C. About half way through the chlorination, the reaction mixture was put under approximately 12" Hg vacuum to encourage removal of hydrogen chloride. Once the desired weight of chlorine was added, the reaction mixture was stirred for 25 minutes before filtering at 28° C. The filtration was very fast. The filter cake was washed with acetic acid. The combined filtrate and wash was set aside for recycle. The product was dried and there was thus obtained 100.9 parts of 82.3% yield of 2,6-dichloro-4-nitroaniline. The DCNA assays 97.3% with 1.6% of the 2-chloro-4-nitroaniline and 0.3% of the 2,4-dichloro-6-nitroaniline.

Example 3

A slurry of 90.2 parts p-nitroaniline in 567 parts of effluent from Example 2 was stirred in a 1 liter round bottomed flask, equipped with a thermocouple, a mechanical stirrer, a sparge tube and a vent system. Chlorine gas (92.4 parts) was sparged into the mixture while the temperature was maintained at about 30° C. The reaction mixture was cooled and the filter cake was washed 4 times with 35 parts of glacial acetic acid. The product was dried and there was thus obtained 116.1 parts or 86.5% yield of 2,6-dichloro-4-nitroaniline.

Example 4

A slurry of 67.4 parts 4-nitroaniline in 782 parts glacial acetic acid was stirred in a 1 liter round bottomed flask, equipped with a thermocouple, a mechanical stirrer, a sparge tube and vent system. Hydrogen chloride gas (21.7 parts) was added via the sparge tube. Chlorine gas (67.5 parts) was sparged into the mixture while cooling to maintain the temperature at 30° C. The bright yellow slurry was then cooled to 20° C. before filtering. The filter cake was washed and the product was dried in vacuo. There was thus obtained 79% or 80.2 parts of 2,6-dichloro-4-nitroaniline of >99% purity by capillary g.c. analysis with a melting point of 190°-194° C.

Example 5

A slurry of 67.8 parts p-nitroaniline in 700 parts of effluent from Example 4 and glacial acetic acid to total 800 parts was stirred in a 1 liter round bottomed flask, equipped with thermocouple, mechanical stirrer, a sparge tube and a vent system.

Chlorine (70.6 parts) was sparged into the mixture while cooling to maintain the temperature at about 30° C. The reaction mixture was then cooled to 20° C. and filtered. The filter cake was washed. There was thus obtained 93.2 parts or 89.1% yield of 2,6-dichloro-4-nitroaniline.

Example 6

A slurry of 67.9 parts p-nitroaniline in 651 parts of effluent from Example 5 and glacial acetic acid to total 800 parts were stirred in a 1 liter round bottomed flask, equipped with a thermocouple, a mechanical stirrer, a sparge tube and a vent system. Chlorine gas (70.9 parts) was sparged into the mixture while cooling to maintain the temperature at about 30° C. The reaction was then cooled to 20° C. and filtered and the resulting filter cake was washed with acetic acid. The product was dried and there was thus obtained 91.8 parts or 90.6% yield of 2,6-dichloro-4-nitroaniline.

What is claimed is:

1. A process for the chlorination of a substituted or unsubstituted nitroaniline by reaction with $Cl_2$ in a reaction medium consisting essentially of acetic acid.

2. A process according to claim 1 wherein said nitroaniline is a compound of the formula:

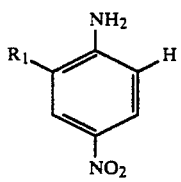

wherein $R_1$ is chloro or hydrogen.

3. A process according to claim 1 wherein $Cl_1$ is added in gaseous form or dissolved in glacial acetic acid.

4. A process according to claim 1 wherein the mole ratio of reactants is about 0.95 to about 2.2 mol $Cl_2$ per mol of the nitroaniline.

5. A process according to claim 1 wherein the mole ratio of the reactants is about 1.9 to about 2.0 mol $Cl_2$ per mol of the nitroaniline.

6. A process according to claim 1 wherein the chlorination is carried out at a temperature of from about 16° C. to about 100° C.

7. A process according t claim 1 wherein the chlorination is carried out at a temperature of from about 20° C. to about 65° C.

8. A process for the chlorination of substituted or unsubustituted nitroaniline the preparation comprising:
  A) reacting a substituted or unsubustituted p-nitroaniline with $Cl_2$ in a reaction medium consisting essentially of acetic acid.
  B) recycling the effluent resulting from said reaction into a reactor and adding sufficient acetic acid to bring the acetic acid concentration of said effluent to at least about 15 weight percent.
  C) reacting a substituted or unsubstituted nitroaniline with $Cl_2$ in the effluent produced in Step B).

9. A process according to claim 8 wherein the acetic acid concentration in Step B) is at least about 90 weight percent.

10. A process according to claim 8 wherein said nitroaniline is a compound of the formula:

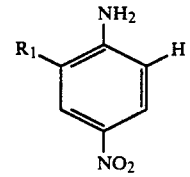

wherein $R_1$ is chloro or hydrogen.

11. A process for the manufacture of 2,6-dichloro-4-nitroaniline by chlorination of para-nitroaniline with $Cl_2$ in a reaction medium consisting essentially of acetic acid.

12. A process according to claim 11 wherein the chlorination reaction is carried out at a temperature of from about 25° C. to about 35° C.

13. A process according to claim 11 wherein the chlorination reaction is carried out at a ratio of about 1.8 to about 2.5 mol $Cl_2$ per mol of nitroaniline.

14. A process according to claim 11 wherein the chlorination reaction is carried out at a ratio of about 1.9 to about 2.0 mol $Cl_2$ per mol of nitroaniline.

* * * * *